United States Patent [19]
Binder et al.

[11] Patent Number: 5,922,184
[45] Date of Patent: Jul. 13, 1999

[54] COMPUTER-DIRECTED DETECTION OF PARAPROTEINS

[75] Inventors: Steven R. Binder, Berkeley; Caroline Scolari, Albany; Robert K. Likuski, Castro Valley, all of Calif.

[73] Assignee: Bio-Rad Laboratories, Inc., Hercules, Calif.

[21] Appl. No.: 08/895,247

[22] Filed: Jul. 21, 1997

[51] Int. Cl.⁶ .................................................. G01N 27/26
[52] U.S. Cl. ............................ 204/452; 702/22; 210/656
[58] Field of Search .................................... 204/451, 461; 7/452, 23, 32; 702/22, 25; 436/516; 382/128, 129; 210/656

[56] References Cited

U.S. PATENT DOCUMENTS

| | | | |
|---|---|---|---|
| 5,098,536 | 3/1992 | Anderson | 204/452 |
| 5,490,909 | 2/1996 | Wang et al. | 204/452 |
| 5,567,282 | 10/1996 | Wang et al. | 204/450 |
| 5,699,157 | 12/1997 | Parce | 356/344 |

FOREIGN PATENT DOCUMENTS 63117257  5/1988  Japan .

OTHER PUBLICATIONS

JAPIO Abstract of Susumu (JP 63117257 A), May 1988.
Lasters et al. ("Background estimation in one–dimensional electropherograms of whole–cell protein extracts", electrophoresis 1985, 6, 508–511) month unavailable.
C.A. Mancuso et al. (Jan. 1986) *Index Medicus* database record, Journal Announcement No. 8607.
J.Y. Yang et al. (Dec. 1991) *Index Medicus* database record, Journal Announcement No. 9207.
P.J. Cardot et al. month unavailable ((1990) *Index Medicus* database record, Journal Announcement No. 9110.
G. Bonnot et al. (Jan. 1, 1995) *Index Medicus* database record, Journal Announcement No. 9507.
H. Cren et al. (May 19, 1993) *Index Medicus* database record, Journal Announcement No. 9311.
S.D. Aird et al. (Aug. 31, 1989) *Index Medicus* database record, Journal Announcement No. 8912.
M.L. Malczewski et al. (Apr. 1981) *Journal of Chromatographic Science* 19: 187–194.
D.W. Kirmse et al. (Jul. 1971) *Analytical Chemistry* 43(8): 1035–1039.
K.A. Barbee et al. month unavailable (1995) *Analytical Biochemistry* 231:301–308.
M.A.A. Kratzer et al. month unavailable (1992) *J. Clin. Pathol.* 45:612–615.
N.M. Papadopoulos et al. month unavailable (1982) *Clin. Chem* 28(4): 707–708.
S. Millership et al. month unavailable (1992) *Computers and Biomedical Research* 25:392–406.
M. Ivandic et al. month unavailable (1996) *Clinical Chemistry* 42 (8) : 1214–1222.

*Primary Examiner*—T. Tung
*Assistant Examiner*—Alex Noguerda
*Attorney, Agent, or Firm*—Townsend and Townsend and Crew LLP

[57] ABSTRACT

Identification and quantification of paraproteins in a sample is achieved by Fourier analysis of mobility-based electropherograms obtained from capillary electrophoresis. The use of a computer algorithm to analyze capillary electrophoresis data, provides the clinician with methods of detecting levels of paraproteins in serum as low as 0.05 g/dL. Additionally, an individual paraprotein can be located on an electropherogram and used to monitor its increased or decreased production in an individual.

13 Claims, 12 Drawing Sheets

COMPUTER-DIRECTED DETECTION OF PARAPROTEINS

BACKGROUND OF THE INVENTION

Serum protein analysis is useful for the diagnosis of lymphoproliferative disease. Gel electrophoresis has been the traditional method of choice for such analysis. Capillary electrophoresis (CE) has also been applied to serum protein analysis. Capillary electrophoresis encompasses a large variety of separation modes, many of which provide separations that equal or exceed the quality of separations that can be performed on slab gels. One form of capillary electrophoresis that is particularly suitable and convenient for many separations is capillary zone electrophoresis (CZE). Other forms include capillary isoelectric focusing, capillary gel electrophoresis, capillary isotachophoresis, micellar electrokinetic chromatography, and capillary electroosmotic chromatography. Separations can be performed in relatively short periods of time by using high voltages, since the small diameter and thin wall of a capillary provide efficient removal of the joule heat generated by the voltage. Detection methods for CE include UV absorbance, fluorescence, electrochemical, Raman, and mass spectrometric.

In gel electrophoresis, the stained gel generally contains a pattern consisting of a series of dark bands on a light background. This gel response can be scanned to find the absorbance at a series of x positions on the gel, creating a potentially quantifiable response. This resulting response is called a densitometer trace.

A response with an x-axis of migration time is typically the data obtained from the capillary electrophoresis experiment. The migration time axis can be changed to normalized mobility by: 1) taking the reciprocal of migration time, 2) multiplying by an appropriate constant, 3) zero correcting by subtracting the electroosmotic velocity, 4) dividing by the zero corrected mobility of a charged marker, and 5) multiplying by a constant, preferably −1. This process gives a more stable x-axis, normalized mobility, allowing far more precise identification and quantitation of the electropherogram components. The appearance of this normalized data set also more closely resembles that of the analogous gel electrophoresis densitometer trace, a shape that is familiar to clinicians.

The gel densitometric or capillary electrophoretic response obtained from a normal human serum proteins sample is a series of relatively broad bands, due to the heterogeneity of the proteins species. Paraproteins, which are homogeneous, will typically be located in a very narrow, dense band on the gel. This narrow band is referred to as a "zone of restricted mobility." On the densitometric scan or in a CE experiment, a paraprotein will show up as a sharp peak in the midst of a broader response, while in the stained gel, the paraprotein will show up as a narrow dark band within a broader one. Visual inspection of the gel electrophoretic response pattern is a very subjective, technique-dependent, and labor-intensive method to detect paraproteins, but has typically been the method of choice for gel electrophoresis. The densitometric trace may also be examined for paraproteins, but this method has proven less sensitive than direct visual inspection of the gel.

Monitoring paraprotein production is necessary to detect and treat diseases, such as multiple myeloma. An individual suffering from multiple myeloma will produce one or more abnormal immunoglobulins in large amounts. The abnormal protein is a paraprotein which, if detected at an early stage, allows an aggressive treatment plan to be employed. Left undetected, a more extreme therapy may be required. Thus, it is important to properly detect paraproteins at as low a level as possible. Large levels are easily detected with the naked eye on either a slab gel or a capillary electrophoresis electropherogram, but low level production of paraproteins are not as easily detected. An automated analysis for paraproteins in capillary electrophoresis has increased sensitivity over the densitometric response, while requiring less time and expertise than direct inspection of gels.

Prior to the discoveries underlying the present invention, methods of paraprotein analysis have simply indicated the presence of paraproteins as a plus/minus. A method that also reports suspected position(s) of paraproteins will allow easier detection, identification, and monitoring of the levels of paraprotein production in an individual.

SUMMARY OF THE INVENTION

It has now been discovered that paraproteins can be detected (identified and quantified) in a serum sample using a Fourier analysis of a capillary electrophoresis data set. The methods of the present invention utilize a software algorithm employing Fourier analysis to detect the presence of a zone of restricted mobility and return an estimate of the position of suspect features. The methods described herein are capable of detecting paraproteins at concentrations as low as 0.05 to 0.1 g/dL. This concentration is considered clinically significant, but can be easily missed by visual inspection of an electropherogram which has not been processed by the methods herein.

In one aspect, the present invention provides methods of detecting the presence or absence of paraproteins in a serum protein sample, by;

(a) separating components in a serum protein sample using capillary electrophoresis to generate a first data set;

(b) subjecting at least a portion of the first data set to Fourier Analysis to generate a forward-transformed data set;

(c) selecting any forward-transformed data sets having high frequency components above a first preselected threshold;

(d) filtering and back-transforming data sets selected in step (c) to provide filtered, back-transformed data sets;

(e) identifying the magnitude and location of residual maxima in the filtered, back-transformed data sets; and (f) comparing the location of any residual maxima having a magnitude above a second preselected threshold to a corresponding location in the first data set to detect the presence of paraproteins in the protein serum sample.

Preferably, the first data set is normalized mobility data. Employing the normalized mobility data and Fourier analysis, the location and a threshold concentration of paraproteins in a serum sample can now be consistently determined by computer algorithm. Thus, the method of this invention provides more information than was previously available and by more consistent methods than previously used.

These and other features, benefits and advantages of the invention are explained in further detail below.

BRIEF DESCRIPTION OF THE DRAWINGS

FIG. 1 is a set of four graphs which provide an illustration of serum protein analysis and the difficulty of detecting the presence of paraproteins. The paraproteins of interest in this invention are typically in the gamma region, but can occur in the beta region also. The gamma region is that region from approximately +0.05 to −0.25 on the x-axis, which represents normalized mobility. The beta region is that region of the x-axis extending from approximately −0.25 to −0.4.

FIG. 2 is a set of four graphs which provide an illustration of the data sets produced and used in analyzing a normal serum protein sample by the method of the present invention. FIG. 2A represents the final result showing no paraprotein regions. FIG. 2B represents a forward transformed data set. FIG. 2C represents the back-transform of the data in FIG. 2B after it has been filtered to exclude the low frequency part. FIG. 2D is a comparison between the original data and a back-transform of the low frequency part that was excluded in FIG. 2C. Although not apparent for the y-axis scale used in FIG. 2D, the difference between the two plots in FIG. 2D will yield the plot in FIG. 2C.

FIG. 3 is a set of four graphs similar to those in FIG. 2 which have been derived from data sets for an abnormal serum protein sample containing paraproteins. FIG. 3A represents the final result showing asterisks where paraprotein regions are located. FIG. 3B represents a forward transformed data set which has been plotted as a power spectrum. FIG. 3C represents the back-transform of the data in FIG. 3B after it has been filtered to exclude the low frequency part. FIG. 3D is a comparison between the original data and a back-transform of the low frequency part that was excluded in FIG. 3C. The difference between the two plots in FIG. 3D will yield the plot in FIG. 3C.

DETAILED DESCRIPTION OF THE INVENTION AND PREFERRED EMBODIMENTS

General

Figure 1A:
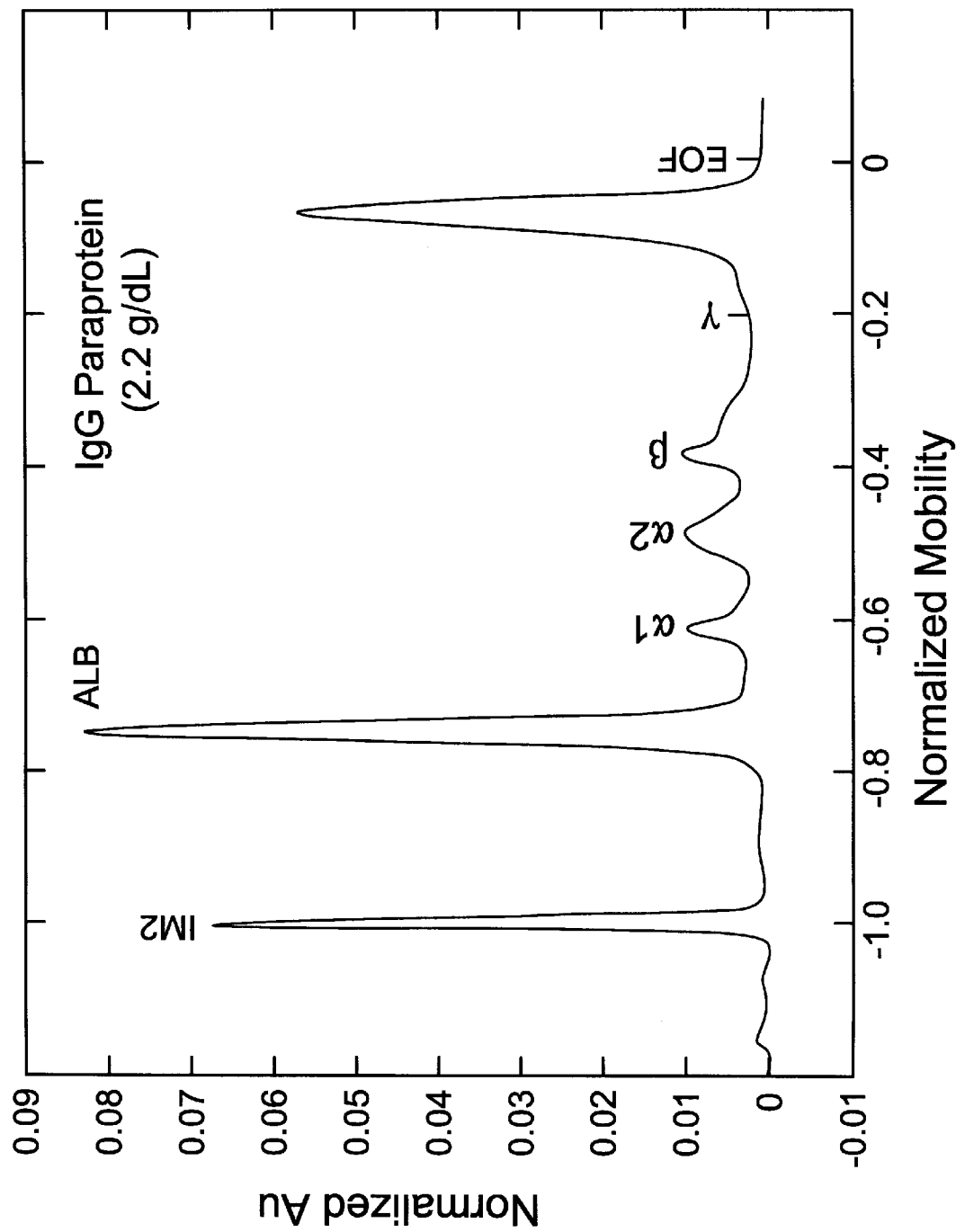
FIG. 1A is a graph of a known sample containing 2.2 g/dL of IgG.
Figure 1B:
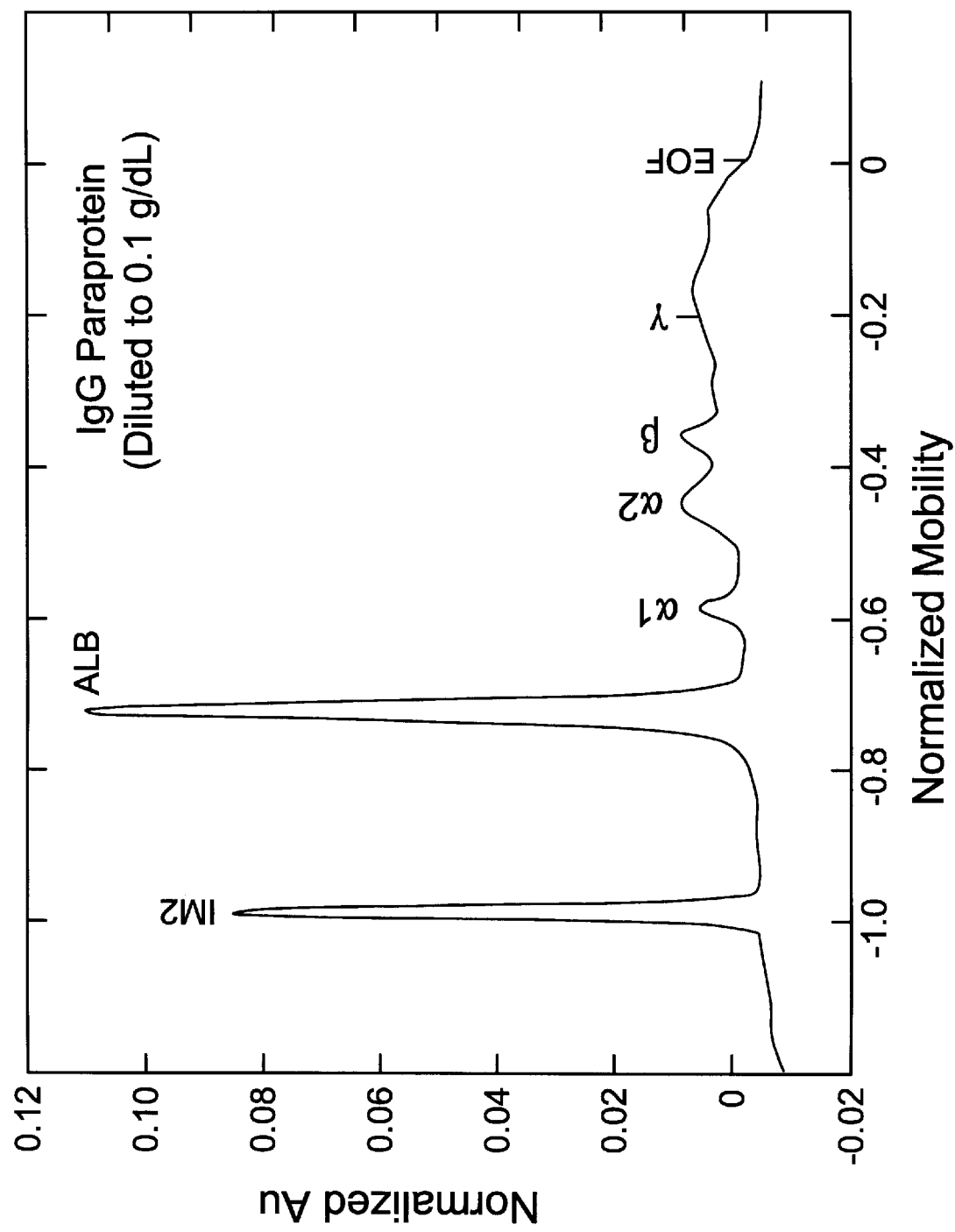
FIG. 1B shows the same paraprotein at a concentration of 0.1 g/dL.
Figure 1C:
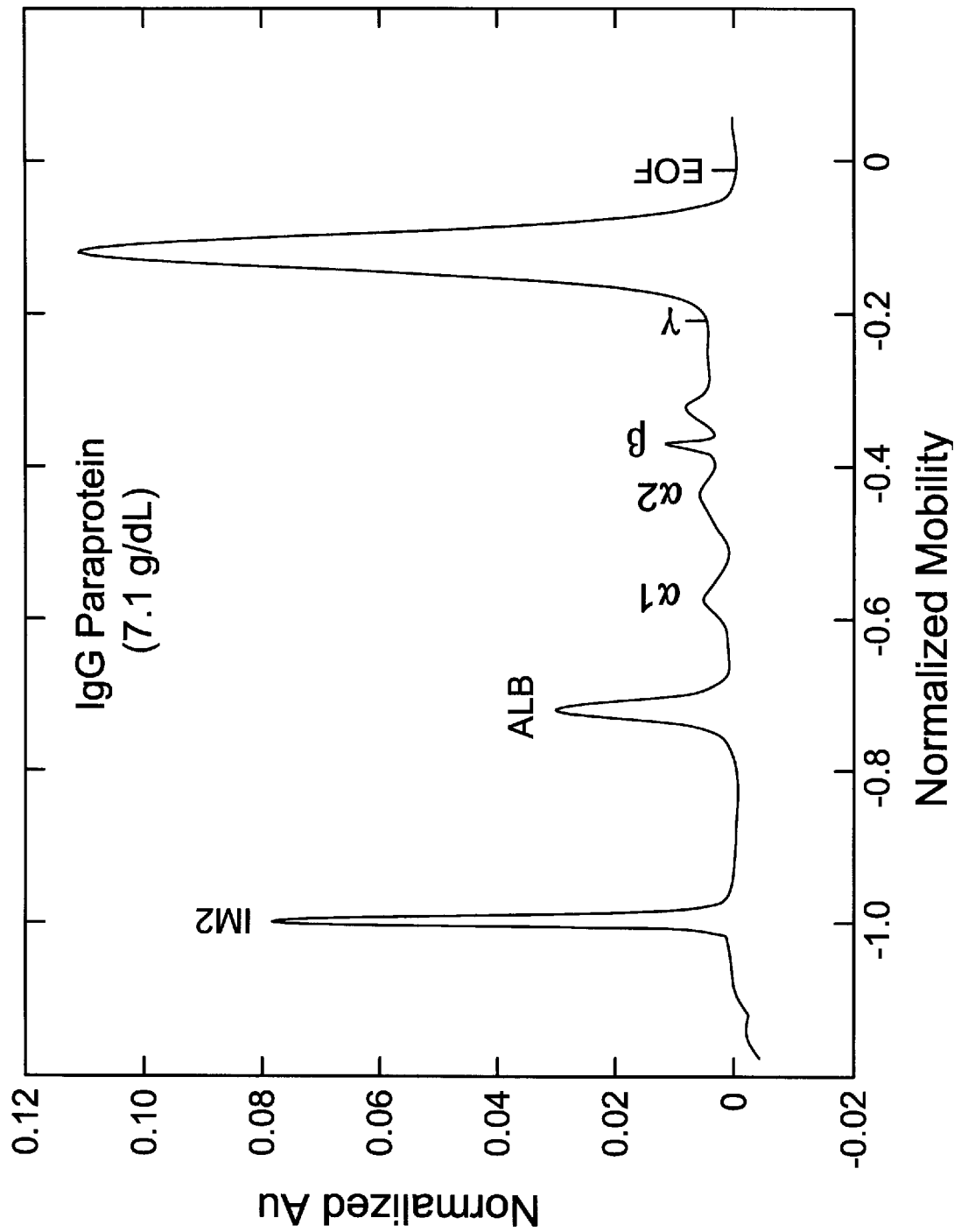
FIG. 1C illustrates a sample containing 7.1 g/dL of a different IgG paraprotein.
Figure 1D:
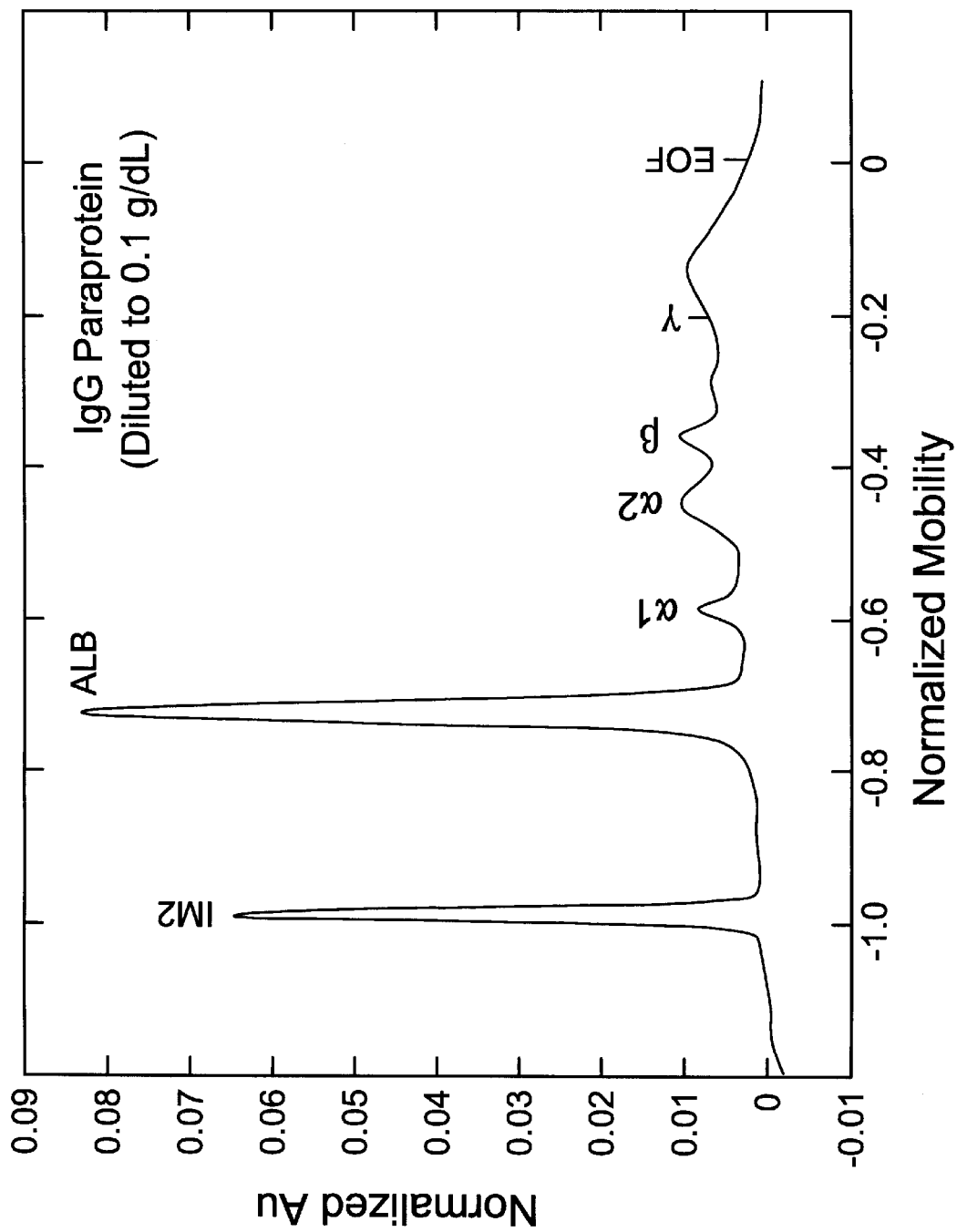
FIG. 1D shows a lower concentration (0.1 g/dL) of the same IgG paraprotein.

The detection and quantitation of paraproteins is used for the detection of multiple myeloma, and in evaluating the course of the disease and response to treatment. The visual detection of low levels of paraproteins provides difficulties for the person unskilled in the examination of electropherograms. This is best illustrated with reference to FIG. 1.

FIG. 1 is a set of four graphs which provide an illustration of serum protein analysis and the difficulty of detecting the presence of paraproteins. The paraproteins of interest in this invention are typically in the gamma region, but can occur in the beta region also. In the examples shown in FIG. 1, the gamma region extends from +0.05 to −0.25 normalized mobility units. The beta region extends from −0.25 to −0.4 normalized mobility units. FIG. 1A illustrates a graph of a known sample with 2.2 g/dL of IgG. The large paraprotein peak in the gamma region of the spectrum can be easily detected by visual examination. FIG. 1B shows the same paraprotein diluted to a concentration of 0.1 g/dL. The gamma region peak at this low concentration is not easily distinguished visually. Similarly, FIG. 1C illustrates a high concentration sample of a different IgG paraprotein. The paraprotein peak at about −0.15 on the x-axis can be easily detected by visual inspection. FIG. 1D shows a lower concentration (0.1 g/dL) of the same IgG paraprotein which is again difficult to detect visually. As the Figures indicate, the consistent visual detection of low levels of paraproteins can be difficult, at best.

The automated detection of paraproteins is facilitated by the fact that paraprotein responses result from the manufacture of a larger than normal amount of a single species in response to a tumor, leading to a sharp response. The normal serum proteins response is the result of a heterogeneous mix of proteins, which leads to a smooth response. Thus, the homogeneous component produces a locally sharper response in the normally smooth serum proteins response.

Thus, differences in the frequency characteristics between the two types of response may be used for purposes of detection. Sharper peaks are expected to contain more high frequency components than smooth peaks. The frequency characteristics of a selected serum proteins region of interest (usually the gamma region), is examined using Fourier analysis. The signal of interest is interpolated to provide $2^N$ equally spaced data points, a fast Fourier transform of the data is taken, and the power spectrum is constructed by multiplying the forward transform of the signal by its complex conjugate. The proportion of signal in the power spectrum occurring in a defined high frequency range is calculated. This calculation can involve different weightings of values over different frequency regions. If the proportion of high frequency signal exceeds threshold, the possibility exists that a high-frequency component (paraprotein) is present.

If an amount of high frequency signal above threshold is found, then an additional step is carried out to ascertain the location of the high frequency region(s) in the scan. The forward transformed data is separated into two parts: a high frequency part and a low frequency part. Back-transforming the low frequency part gives a smoothed data set which can be subtracted from the original (first) data set to provide a residual data set. Back-transforming the high frequency part provides the residual data set directly. Residual segments are defined and examined, and the maximum height of each residual segment is found. If the maximum positive deviation of the residual segment exceeds threshold, this location of maximum deviation is stored as a possible site of paraprotein. This step has two purposes. First, it weeds out some false positives found upon examining the power spectrum alone. Second, this step gives an estimate of the location of possible high frequency (paraprotein) features.

However, some false positives can make it through both of these steps. For example, a sudden change in shape at the end of a delimited region, due to an improperly placed delimiter, can contribute high frequency components to the power spectrum, and produce fairly large residuals at the ends of the delimited region under examination. To prevent these end segments from triggering false positives, a verification of the residual results is performed.

The verification of results found by Fourier analysis is accomplished using a feature pick algorithm used in CDM 2.0 software (available from Bio-Rad Laboratories). A paraprotein response is expected to appear as either a crest or a shoulder. Thus, shoulders and crests found by the feature pick algorithm in the time domain are valid features of interest. This time domain information is also available in normalized mobility units. The location of the valid feature (s) found in the time domain is checked versus the location of the valid residual deviation(s) found through Fourier analysis. If a feature found by this independent check matches the location of a found residual segment maximum within a specified threshold (0.05 normalized mobility units, for example), a paraprotein is considered detected, and the x-location of the paraprotein is taken to be the location of the feature(s) found by the peak-pick algorithm.

Once the location of paraprotein features are found, the response may be quantified, using either manual delimiting of the area under the response, or by more automated means.

The present invention provides a method of detecting paraproteins using a computer algorithm. The algorithm removes the need to visually inspect difficult spectra such as those in FIGS. 1B and 1D for paraprotein peaks.

EMBODIMENTS OF THE INVENTION

In one aspect, the present invention provides methods of detecting the presence or absence of paraproteins in a serum protein sample, by;

(a) separating components in a serum protein sample using capillary electrophoresis to generate a first data set;

(b) subjecting at least a portion of the first data set to Fourier Analysis to generate a forward-transformed data set;

(c) selecting any forward-transformed data sets having high frequency components above a first preselected threshold;

(d) filtering and back-transforming data sets selected in step (c) to provide filtered, back-transformed data sets;

(e) identifying the magnitude and location of residual maxima in the filtered, back-transformed data sets; and (f) comparing the location of any residual maxima having a magnitude above a second preselected threshold to a corresponding location in the first data set to detect the presence of paraproteins in the protein serum sample.

The components in a serum protein sample are readily separated by capillary electrophoresis using methods well known to those skilled in the art. Capillary electrophoresis facilitates the analysis of small samples using high voltages and relatively short separation times. A preferred form of capillary electrophoresis is "open capillary zone electrophoresis," in which the separation medium is a buffer solution.

Protein separations are readily performed using capillary electrophoresis with conventional capillary electrophoresis units and materials which are commercially available from suppliers such as Bio-Rad Laboratories (Hercules, Calif. USA). Operating conditions and procedures used for the separations are similarly conventional and can be selected and employed using methods known to those of skill in the art. A particularly preferred system for capillary electrophoresis is the Biofocus 2000 with CDM 2.0 software, available from Bio-Rad Laboratories.

The capillaries used for serum protein separation will typically be capillaries of silica containing material, preferably fused silica whose internal surface has not been coated. Other useful capillaries are glass or quartz. The internal diameters of the capillaries will typically be from about 20 µm to about 75 µm. Preferably, the capillaries used are those having internal diameters of about 25 µm to about 35 µm, more preferably about 25 µm. Capillaries of the type noted and preferred for serum protein electrophoresis may be obtained commercially from Bio-Rad. In other embodiments, the present invention will use electrophoretic separations performed in slab-shaped cells and other non-capillary systems.

As noted above, separations of serum components will typically use conditions which are readily determined by those of skill in the art. Preferred conditions are described in co-pending application U.S. Ser. No. 08/610,105, filed Feb. 29, 1996 now U.S. Pat. No. 5,660,701, issued Aug. 26, 1997, incorporated herein by reference. The run buffer will typically be an aqueous solution of glycine with added acid or base. In one group of embodiments, a preferred run buffer is Bio-Rad part #194-5055. Typically, the serum samples are diluted into an aqueous buffer prior to injection into the capillary. The diluent may be the run buffer, or it may be a lower conductivity solution to provide a higher resolution through a process known as stacking. The diluent may also contain internal standard(s) for calibrating the y-axis or markers for calibrating the x-axis. Hippuric acid or xanthine may be used as an internal standard, as a marker, or both. The preferred sample diluent is Bio-Rad part #194-5056.

After introduction of the diluted sample into the capillary, a voltage is applied and the sample is separated into its various components. For capillary systems, separations will be carried out using voltages of about 1 kV to about 30 kV, preferably about 5 kV to about 15 kV. The components are resolved into bands, which migrate along the capillary and past the detector.

Detection of the bands of proteins can be achieved by any method that is known to be applicable to capillary electrophoresis. One type of detection is ultraviolet absorbance detection. Direct UV-absorbance detection can be achieved by passing a UV beam through the capillary, transverse to the capillary axis, and continuously monitoring the intensity of the beam emerging after having been interrupted by solute zones migrating across its path.

Detection of the component species (e.g., proteins in a serum sample) provides a first data set. In some embodiments, the data can be used to plot an electropherogram. Alternatively, the first data set can be subjected to further analysis to generate an electropherogram capable of computer manipulation for area and peak height determination, normalization and zero correction.

After detection, the data is generally transferred to a digital processor (often a personal computer) as a series of digital amplitudes. The first amplitude is generally given an index number of zero or one. The index is generally incremented by one for each subsequent amplitude. For further analysis and/or presentation, the indices are converted to a more appropriate quantity with corresponding units, e.g., migration time in minutes.

A first data set obtained by the methods and of the type described above is preferably mobility zero corrected and normalized according to the methods in copending application U.S. Ser. No. 08/866,282, filed May 30, 1997 (Attorney Docket Number 2558B-590), incorporated herein by reference.

The first data set, which is preferably zero corrected and converted to normalized mobility, is subjected to a Fourier analysis (including Fourier transformation of the data) or another mathematically equivalent method to provide a forward-transformed data set. Fourier transformation is a well-known mathematical process for the conversion of time or position data into frequency data. All of the first data set can be transformed at this point or just that portion which represents a paraprotein region. In a delimited data set, the limits are typically set at 0 to −0.4 and more preferably at 0 to −0.3. The delimited portion will typically correspond to the gamma region, but could also correspond to the beta region. The forward-transformed data set thus generated can be used to construct a power spectrum for visual examination.

To determine whether the distribution of the power spectrum response over frequency indicates the presence of a paraprotein, a high frequency region and a low frequency region are defined. The boundaries between the low frequency region and the high frequency region can be defined as an abrupt transition or a gradual transition. It has been found that a linear transition is both convenient and suitable. Because of noise, detection is improved by limiting the extent of the high frequency region examined. This upper boundary may also be gradual or abrupt. If the high frequencies have already been excluded by prior filtering, the results are not sensitive to the upper boundary. By altering the transition points, all high frequencies can be examined, or a smaller subset. Typically, a lower transition from 0.002 to 0.004 normalized frequency units, and an upper transition from 0.014 to 0.016 normalized frequency units are used. Those components above the preselected threshold are selected and labeled as possible abnormal regions. The preselected area threshold will typically be set at about $1\times10^{-4}$ to about $1\times10^{-2}$, and more preferably at about $1\times10^{-3}$. The thresholds are typically set to levels corresponding to concentrations of about 0.05 to about 0.1 g/dL.

The forward transform data set is next filtered and back-transformed. Back-transformation is the reverse operation of Fourier transform. For example, if Fourier transforms are used to convert data from the time domain to the frequency domain, then a back-transform will convert the data from the frequency domain back into time. If the data has not been filtered, the back-transform will restore the original data set.

Filtering emphasizes those frequency components of interest. The forward transformed data is multiplied by a function designed to keep those frequencies of interest, and de-emphasize those frequencies not of interest. Commonly, filtering is used to separate the data into high frequency parts and low frequency parts. The transition between a low frequency region and high frequency region may be gradual or abrupt. Filters using a linear ramp in the transition region are convenient and suitable for this purpose. Filters typically used include low pass filters, high pass filters, bandpass filters, notch filters, or combinations thereof. Preferably, the filters used are high and low pass filters. In some embodiments, the filter used is a ramp smoothing filter. In other embodiments, a square smoothing filter is used.

If a filter is applied and the data set is then back-transformed, the back-transformed data will no longer match exactly the original data set. If a low pass filter has been applied, the back-transformed data set will be smoothed. If a high pass filter has been applied, the back-transformed data set will be a residuals data set. The same residuals data set may also be constructed by subtraction of the smoothed data set from the first (original) data set.

The Fourier transforms and filtering functions can be done using the appropriate software. One example is the MatLab routine named FFT from the MatLab programming environment (Math Works, Inc., Natick, Mass., USA).

The filtered, back-transformed data set can then be examined for the presence (magnitude and location) of residual maxima. These residual maxima correspond to potential paraprotein sites. Any residual maxima having a magnitude above a preselected threshold is considered to be the potential site of a paraprotein. The amplitude threshold is typically set at $1\times10^{-5}$ to $1\times10^{-2}$ normalized AU, and more preferably at about $1\times10^{-4}$ normalized AU. The amplitude threshold is typically set to levels corresponding to concentrations of about 0.05 to about 0.1 g/dL.

The data can be analyzed under various filter conditions, and if paraproteins are found using specified filtering conditions, the area can be identified as a paraprotein region. To verify the assignment, the results of an independent feature-pick routine are used to confirm that a feature exists in the predicted location. An example of this independent feature pick routine is the peak detection algorithm in CDM 2.0 software, available from Bio-Rad Laboratories which selects valid shoulders and crests in the time domain. This time domain information is also available in normalized mobility units. The location of these features found in the time domain is checked versus the location of the valid residual deviation(s) found through Fourier analysis. If a feature found by this independent check matches the location of a found residual segment maximum within a specified threshold (0.05 normalized mobility units, for example), a paraprotein is considered detected, and the x-location of the paraprotein is taken to be the location of the feature(s) found by the peak-pick algorithm.

In this manner, through a combination of power spectrum high frequency region examination, construction and examination of residual maxima, and verification using an independent feature-pick routine, the detection of paraproteins above a threshold concentration may be accomplished and the location determined. These paraproteins can then be quantified manually or automatically and monitored for change in an individual.

A pictorial representation of the present method is provided in FIGS. 2 and 3 for a normal and an abnormal serum sample. Each of the figures is a compilation of four graphs which represent delimited data sets, power spectra, residual spectra and a comparison of a filtered, back-transformed data set to the delimited data set. FIG. 2 provides the graphs for data from a normal serum protein sample and FIG. 3 provides the graphs for data from a serum protein sample containing paraproteins. FIGS. 2B and 3B depict power spectra constructed from Fourier transformation of the first data sets generated by the capillary electrophoresis serum protein separation. The data is plotted as normalized response versus normalized frequency. The high frequency region of FIG. 3B has discernably more area than the high frequency region of FIG. 2B. The power spectrum can be used to select components of high frequency regions and to determine the area or relative area under a high bandpass region. This information can be used to determine threshold concentrations.

Figure 2A:
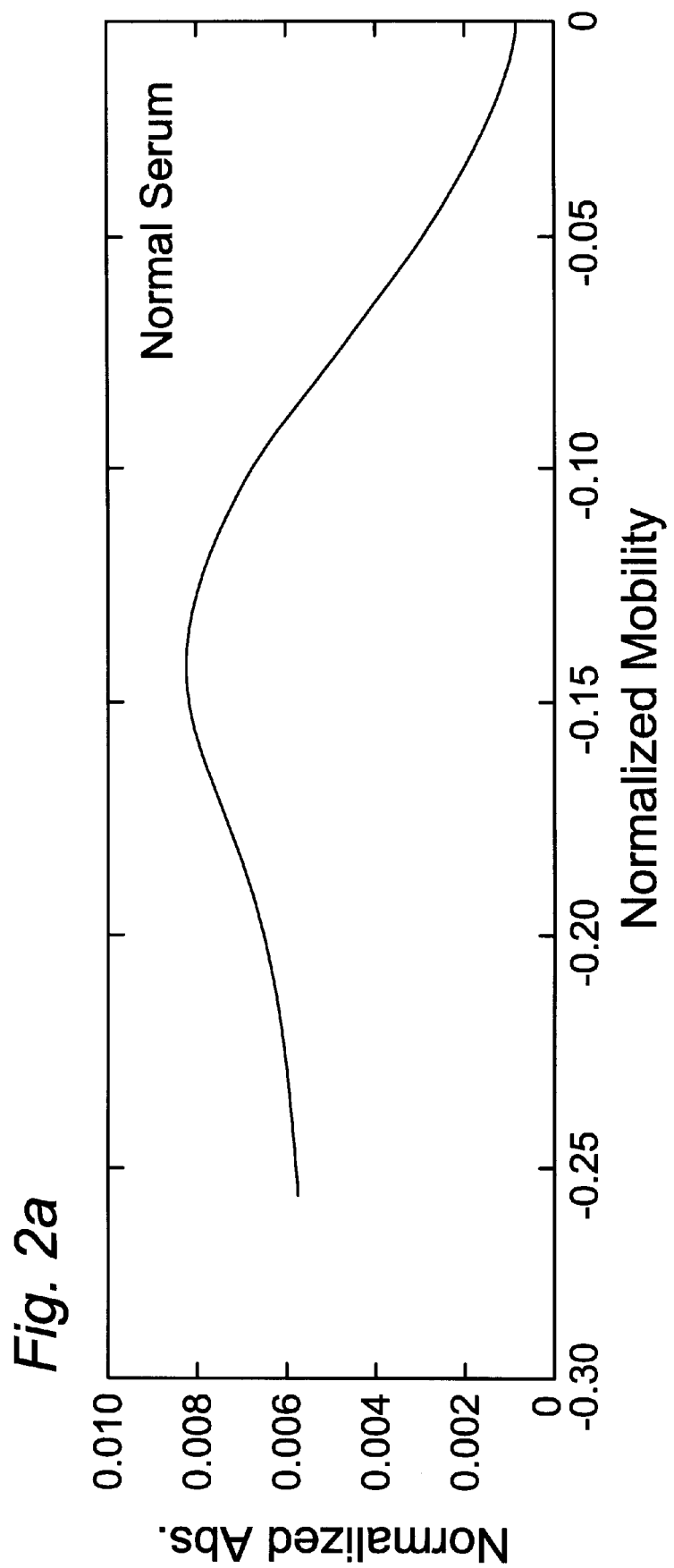
In FIGS. 2A, 2C, and 2D the y-axis is normalized absorbance and the x-axis is normalized mobility.
Figure 2B:
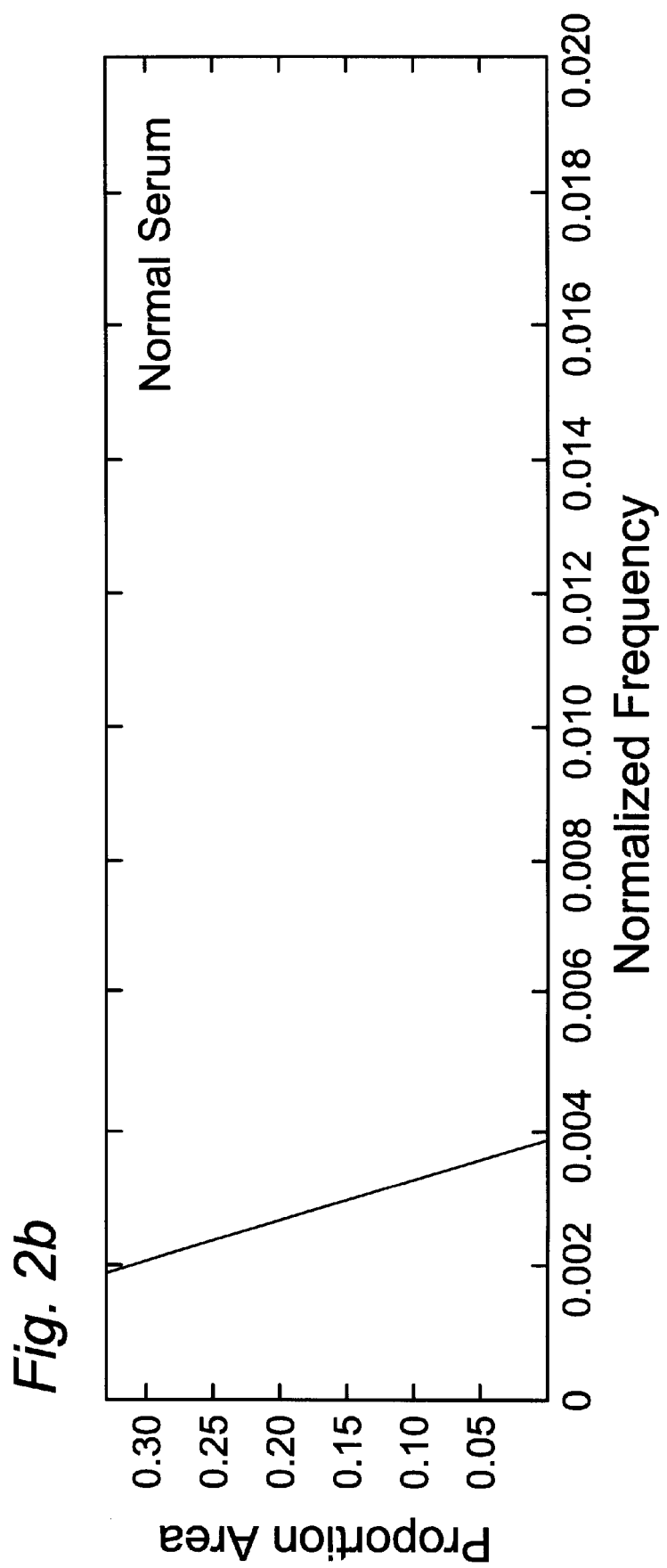
In FIG. 2B, the y-axis is area proportion and the x-axis is normalized frequency units.
Figure 2C:
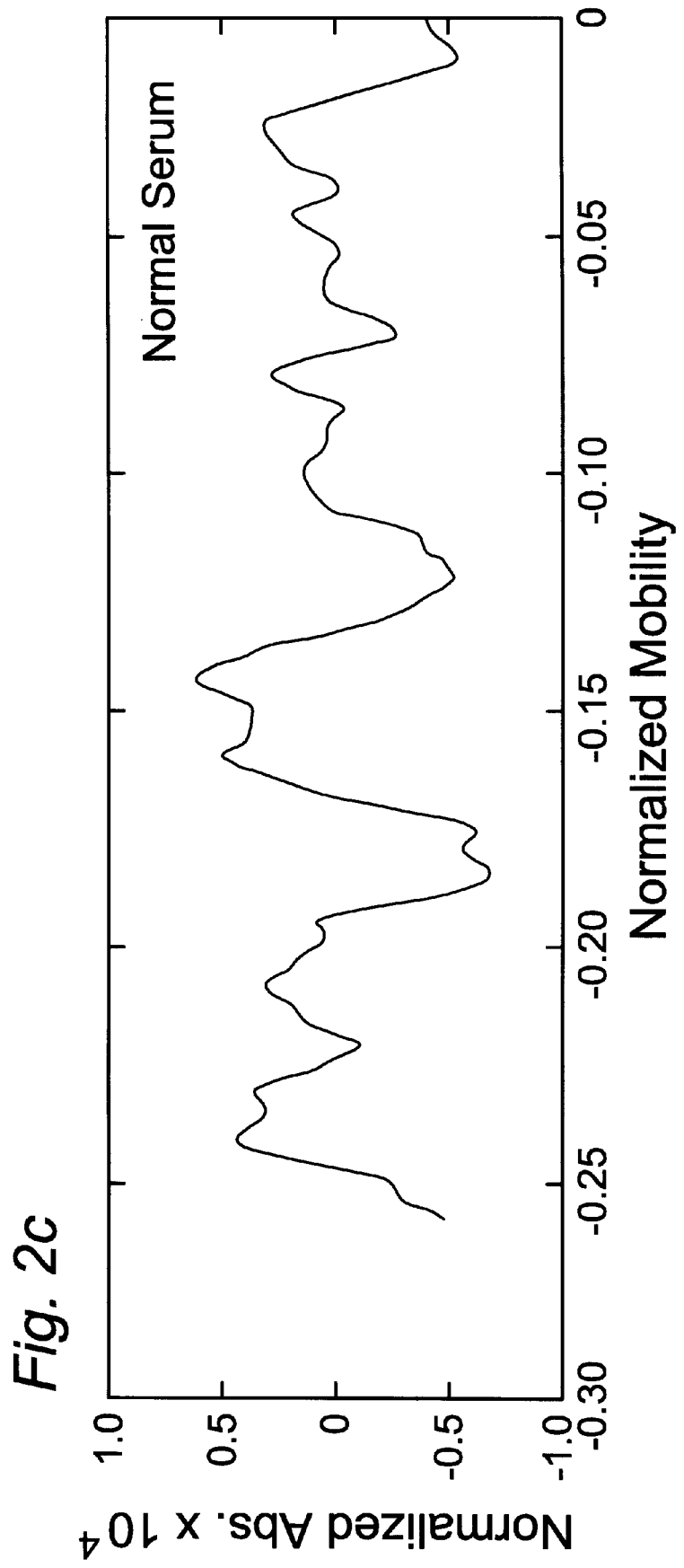

The first data set can also be filtered and back-transformed to produce a smoothed data set, which can then be subtracted from the first data set to produce a residual plot. FIGS. 2C and 3C show plots of the residuals of the filtered back-transformed data subtracted from the first data set. The residuals in FIG. 3C are larger than those in FIG. 2C. The largest residual maximum in FIG. 3C is at the site of the paraprotein response. These plots can be used to determine the locations of any paraprotein regions above the predetermined threshold.

Figure 2D:
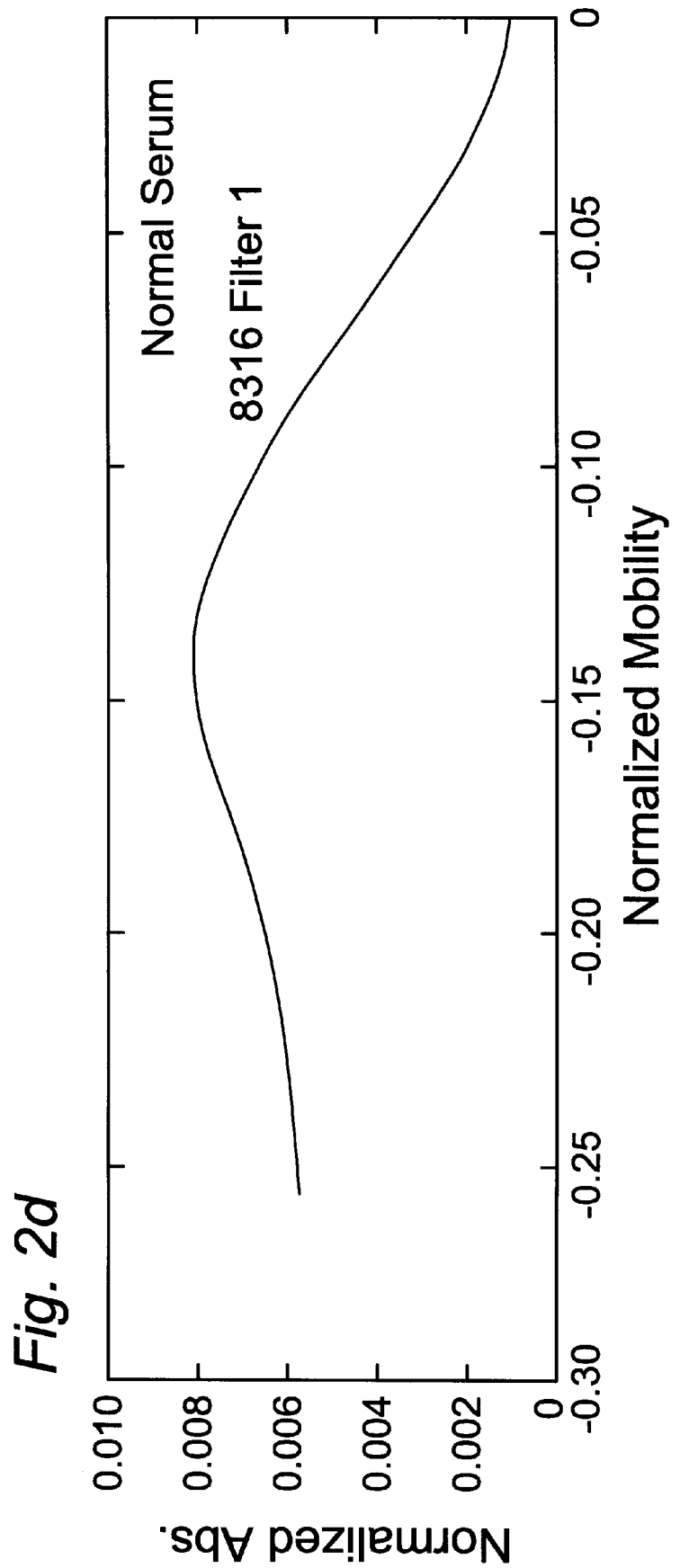
Figure 3A:
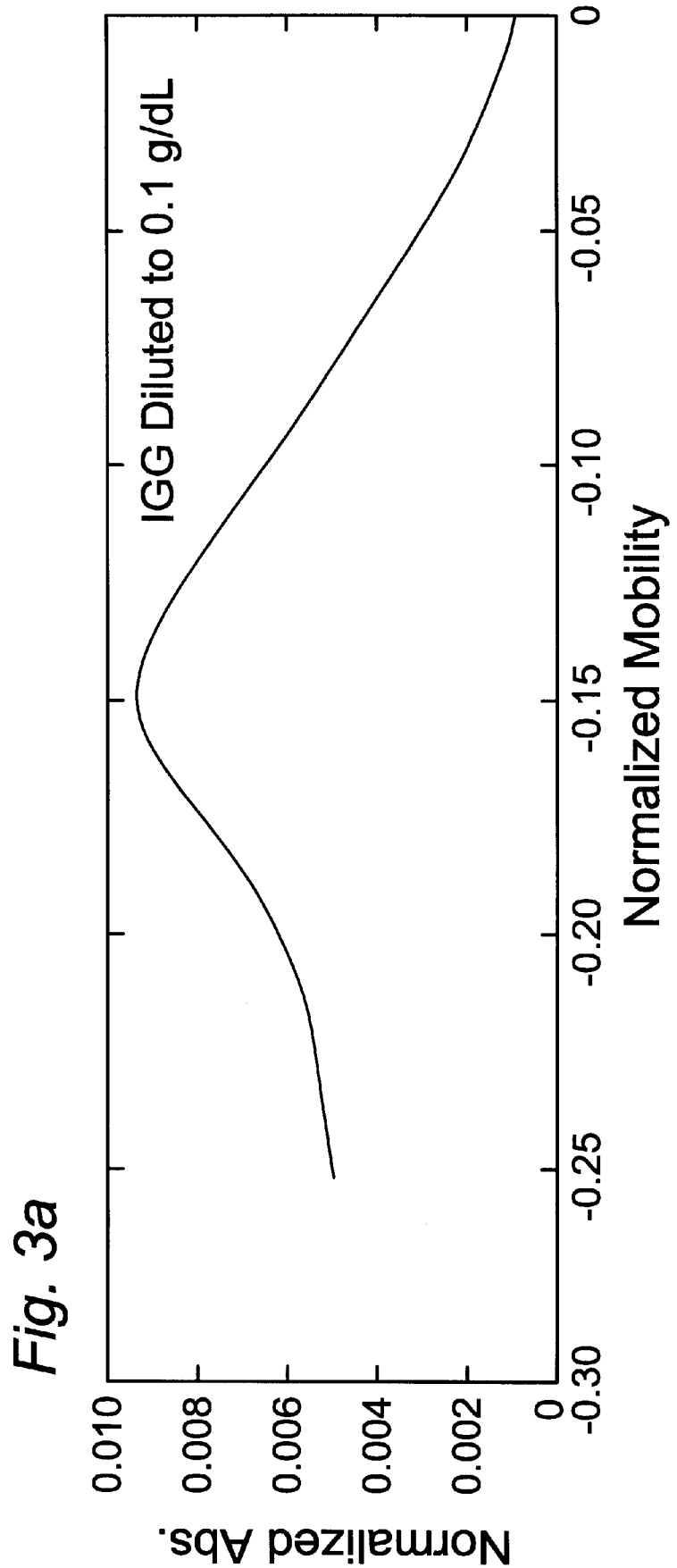
In FIGS. 3A, 3C, and 3D the y-axis is normalized absorbance and the x-axis is normalized mobility.
Figure 3B:
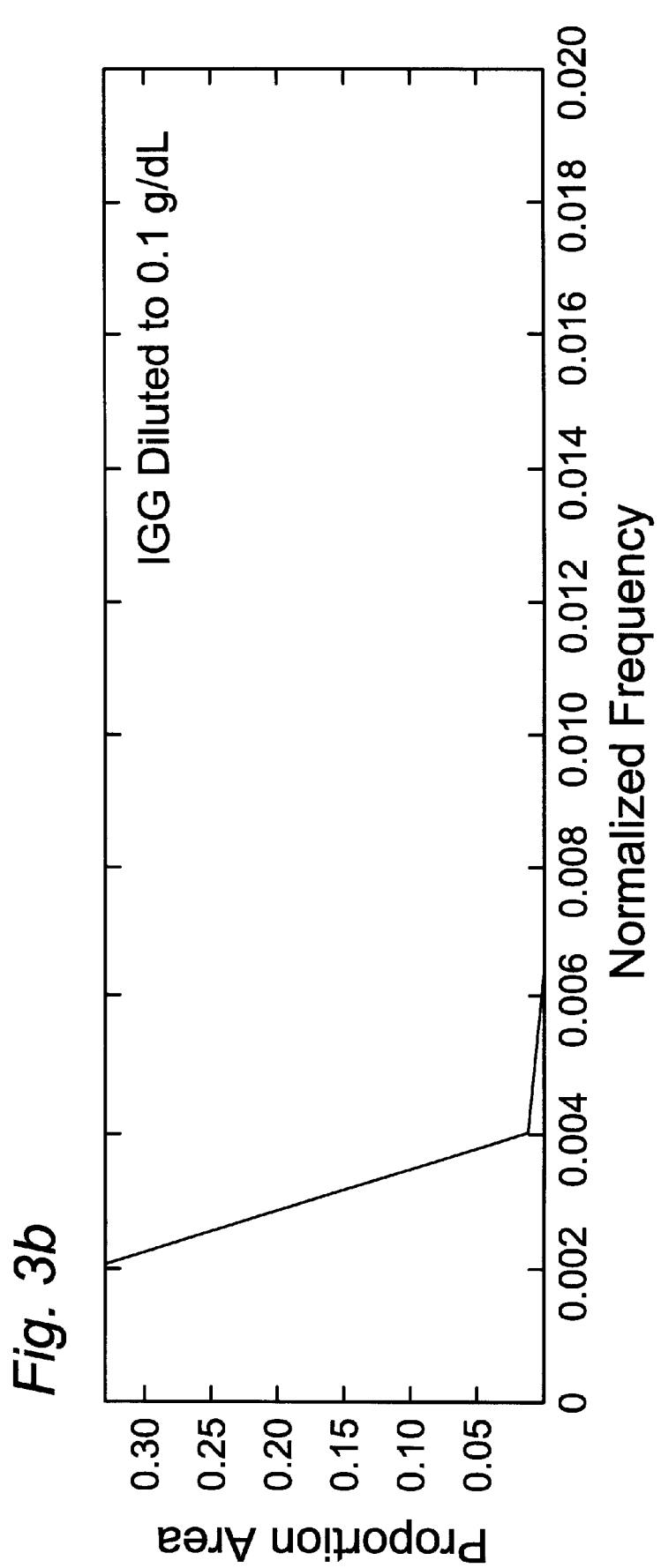
In FIG. 3B, the y-axis is area proportion and the x-axis is normalized frequency units.
Figure 3C:
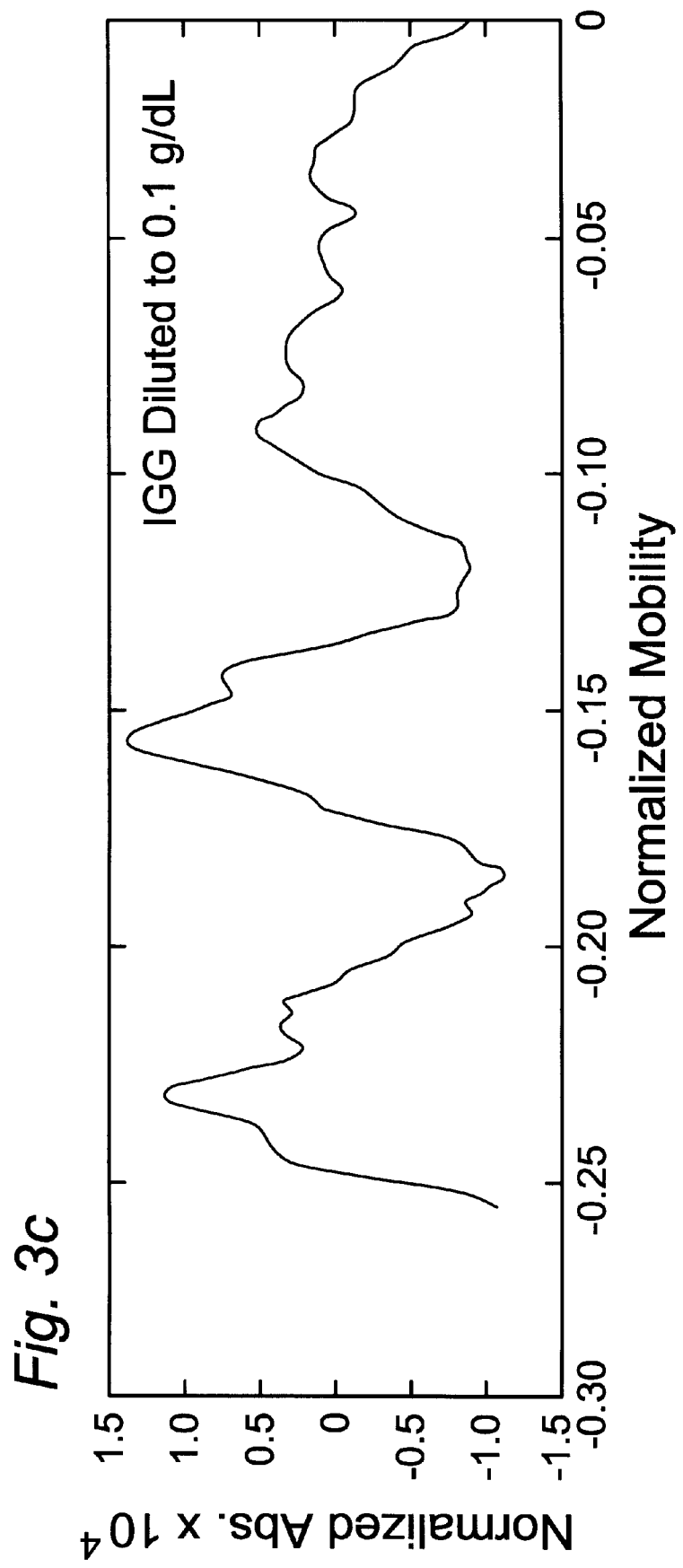
Figure 3D:
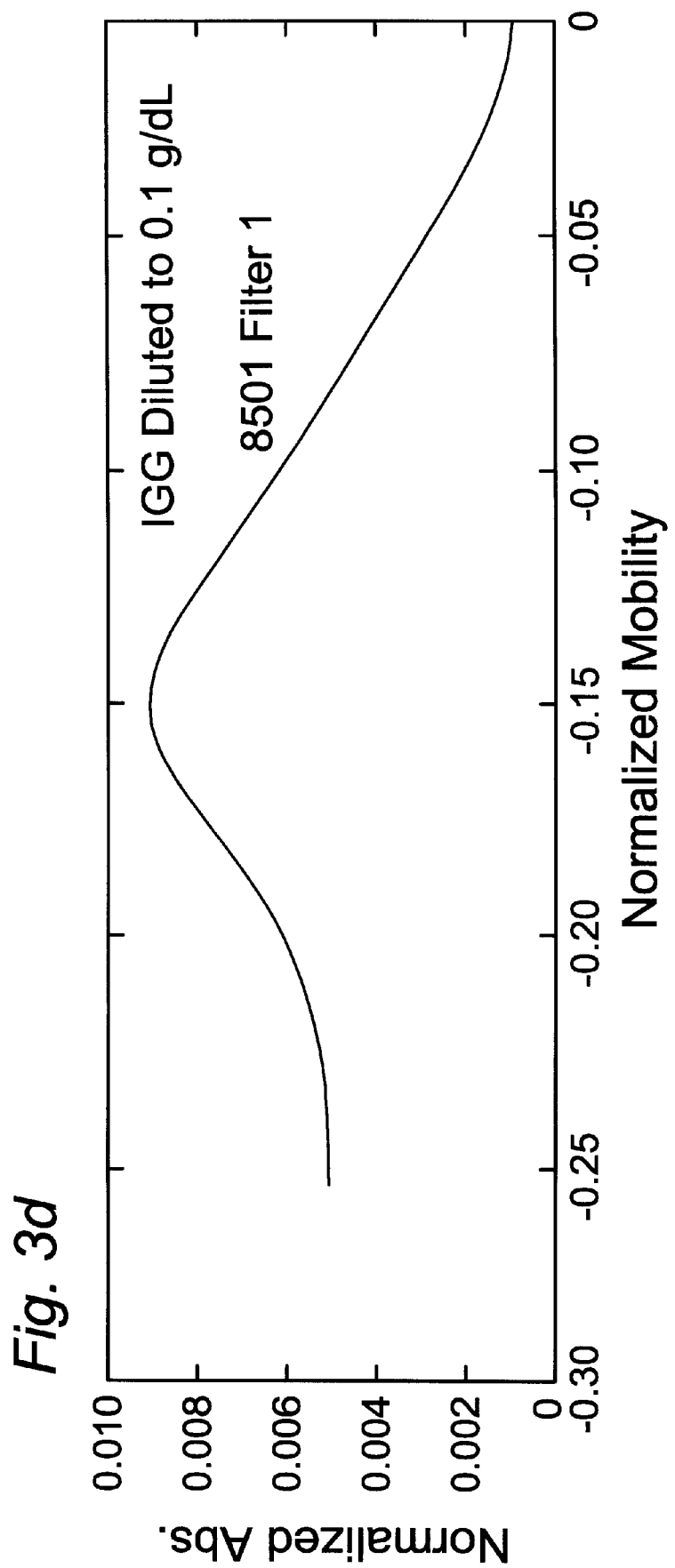

FIGS. 2D and 3D depict the comparisons of the filtered back-transformed data and the first data set with arrows marking the paraprotein regions detected at a concentration above the second threshold. The smoothed back-transformed data from the normal sample in FIG. 2D matches the original data quite closely, while discrepancies may be seen between the smoothed, back-transformed data and the original data from the abnormal sample in FIG. 3D.

FIGS. 2A and 3A depict the final result. A paraprotein was correctly found for the abnormal sample (FIG. 3A) at a normalized mobility of $-0.15$.

The methods of this invention are of greatest interest for the analysis of biological samples, or the detection and/or quantifying of specific components in biological samples.

Typical samples include whole blood, plasma, serum, urine and cerebrospinal fluid. Human serum is one of the most common samples in need of analysis.

Thus, in another aspect, the present invention provides a method of monitoring paraprotein production in an individual, comprising;

(a) subjecting an individual's first serum protein sample to capillary electrophoresis and detecting paraproteins at a first level using the method described above;

(b) subjecting said individual's second serum protein sample to capillary electrophoresis and detecting paraproteins at a second level according to methods above; and (c) comparing the first level and the second level to monitor level of paraprotein production in said individual.

In this aspect of the invention, the comparing can be carried out by a skilled clinician or by computer programs which provide comparison routines, and the calculation of areas from a specific region, such as, for example, CDM 2.0 software, available from Bio-Rad Laboratories.

The following example is offered for purposes of illustration only.

EXAMPLE 1

Four patient sera samples were obtained from a university hospital in a midwestern state. Each of the samples contained a paraprotein, quantified at the hospital using the Beckman Paragon gel at a level above 1.0 g/dL. Two were IgG, one was IgA and the other was IgM.

Each sample was diluted with a pool of normal sera to obtain paraprotein concentrations of 0.5, 0.2, 0.1 and 0.05 g/dL. The samples containing paraproteins at 0.1 g/dL were each run ten times. The neat patient sample and all dilutions were run in duplicate. The normal pool was run four times along with each patient set, twice before and twice after the patient samples. A positive result was indicated by the presence of a "check gamma" message in the sample report.

Positive results were obtained on all the neat, 0.5 and 0.2 g/dL solutions. At the 0.1 g/dL level, 39 of the 40 runs evaluated indicated a positive result. At the 0.05 g/dL level, three of the eight injections had positive results. For the control, only one of 16 injections indicated a positive result (see Table 1).

TABLE 1

| Concentration of Paraproteins | n | Positive* | Negative |
| --- | --- | --- | --- |
| >1.0 g/dL | 8 | 8 | 0 |
| 0.5 g/dL | 8 | 8 | 0 |
| 0.2 g/dL | 8 | 8 | 0 |
| 0.1 g/dL | 40 | 39 | 1 |
| 0.05 g/dL | 8 | 3 | 5 |
| Negative pool | 16 | 1 | 15 |

*Positive indicated by "Check Gamma" message on report.

The foregoing is offered primarily for purposes of illustration. It will be readily apparent to those skilled in the art that the operating conditions, materials, procedural steps and other parameters of the systems and methods described herein may be further modified or substituted in various ways without departing from the spirit and scope of the invention.

What is claimed is:

1. A method of detecting the presence or absence of paraproteins in a serum protein sample, said method comprising;

(a) introducing a serum protein sample into an electrophoresis capillary;

(b) separating components of said sample in said capillary by electrophoresis;

(c) generating a first data set by detecting said separated components;

(d) subjecting at least a portion of said first data set to Fourier Analysis to generate a forward-transformed data set;

(e) dividing said forward-transformed data set into low frequency components and high frequency components;

(f) selecting any forward-transformed data sets having an amount of high frequency components above a first preselected threshold;

(g) filtering said selected forward-transformed data sets to provide filtered data sets;

(h) back-transforming said filtered data sets to provide filtered, back-transformed data sets;

(i) identifying the magnitude and location of residual maxima in said filtered, back-transformed data sets; and (j) comparing the location of any residual maxima having a magnitude above a second preselected threshold to a corresponding location in said first data set to detect the presence of paraproteins in said sample.

2. A method in accordance with claim 1, wherein said first data set is a delimited mobility data set.

3. A method in accordance with claim 1, wherein said first data set is a time data set.

4. A method in accordance with claim 1, wherein said filtering uses filters selected from the group consisting of high-pass filters, low-pass filters, notch filters and combinations thereof.

5. A method in accordance with claim 1, wherein said filtering uses high-pass filters and low-pass filters.

6. A method in accordance with claim 5, wherein said filter is matched to the frequency profile of potential paraprotein regions.

7. A method in accordance with claim 1, wherein said paraproteins are detected at a level above about 50 mg/dL.

8. A method in accordance with claim 1, wherein said paraproteins are detected at a level above about 100 mg/dL.

9. A method in accordance with claim 1, wherein said paraproteins are detected at a level above about 250 mg/dL.

10. A method in accordance with claim 1, wherein said first data set is a delimited mobility data set which is mobility zero corrected and normalized.

11. A method in accordance with claim 1, wherein steps (a)–(i) are performed by automated instrumentation governed by computer software.

12. A method of monitoring paraprotein production in an individual, said method comprising;

(a) subjecting an individual's first serum protein sample to capillary electrophoresis and detecting paraproteins at a first level using the method of claim 1;

(b) subjecting said individual's second serum protein sample to capillary electrophoresis and detecting paraproteins at a second level according to method of claim 1; and (c) comparing said first level and said second level to monitor level of paraprotein production in said individual.

13. A method in accordance with claim 12, wherein said serum protein sample is human serum protein.

* * * * *

UNITED STATES PATENT AND TRADEMARK OFFICE
CERTIFICATE OF CORRECTION

PATENT NO. : 5,922,184
DATED : July 13, 1999
INVENTOR(S) : Steven R. Binder et al.

It is certified that error appears in the above-identified patent and that said Letters Patent is hereby corrected as shown below:

Column 10,
Line 49, change "(a) - (i)" to -- (a) - (j) --.

Signed and Sealed this

Twenty-first Day of September, 2004

JON W. DUDAS
*Director of the United States Patent and Trademark Office*